US007074959B2

(12) United States Patent
Helvenston et al.

(10) Patent No.: US 7,074,959 B2
(45) Date of Patent: Jul. 11, 2006

(54) METHODS AND SYSTEMS FOR REMEDIATING HYDRAZINE-CONTAMINATED EQUIPMENT AND/OR SURFACES

(75) Inventors: Merritt C. Helvenston, Las Vegas, NM (US); Rudolfo A. Martinez, Santa Fe, NM (US); Jose C De Baca, Las Vegas, NM (US); John J. Juarez, Las Vegas, NM (US)

(73) Assignee: New Mexico Highlands University, Las Vegas, NM (US)

( * ) Notice: Subject to any disclaimer, the term of this patent is extended or adjusted under 35 U.S.C. 154(b) by 0 days.

(21) Appl. No.: 10/211,891

(22) Filed: Aug. 1, 2002

(65) Prior Publication Data

US 2004/0024251 A1 Feb. 5, 2004

(51) Int. Cl.
*C07C 243/14* (2006.01)

(52) U.S. Cl. ...................... 564/250; 540/239; 540/492; 544/239; 588/244; 588/246; 562/563

(58) Field of Classification Search ................ 544/239; 540/492, 239; 564/250; 588/244, 246; 562/563
See application file for complete search history.

(56) References Cited

U.S. PATENT DOCUMENTS

| | | | | |
|---|---|---|---|---|
| 4,289,774 | A * | 9/1981 | Schacht et al. | 424/250 |
| 4,783,462 | A * | 11/1988 | Matsukado et al. | 514/249 |
| 4,789,638 | A | 12/1988 | Kramer et al. | 436/111 |
| 4,857,661 | A | 8/1989 | Sung et al. | 562/502 |
| 5,344,546 | A | 9/1994 | Kiesele et al. | 204/415 |
| 5,371,285 | A | 12/1994 | Kondo et al. | 562/441 |
| 5,387,696 | A | 2/1995 | Kottenhahn et al. | 548/533 |
| 6,319,328 | B1 | 11/2001 | Greenberg et al. | 134/2 |
| 6,319,882 | B1 | 11/2001 | Ivey | 510/110 |
| 6,348,468 | B1 * | 2/2002 | Ohkuchi et al. | 514/252.03 |
| 6,398,960 | B1 | 6/2002 | Borden et al. | 210/610 |
| 6,399,611 | B1 * | 6/2002 | Jonas et al. | 514/252 |
| 6,402,952 | B1 | 6/2002 | McMurtrey et al. | 210/634 |
| 2001/0031894 | A1 | 10/2001 | Buchwald et al. | 564/148 |

FOREIGN PATENT DOCUMENTS

| | | | |
|---|---|---|---|
| EP | 0724468 | B1 | 5/1998 |

OTHER PUBLICATIONS

Gerd Kaupp & Jens Schmeyers, "Solid-State Reactivity of the Hydrazine-Hydroquinone Complex," J. Phys. Org. Chem. 2000; 13: pp. 388-394.
William Lagna & Patrick Callery, "Synthesis of d1-Glutamine-2,5-15N2", Jounral of Labelled Compounds and Radiopharmaceuticals—vol. XXI, No. 4, pp. 337-345.
Modec, Inc. "Formulations for the Decontamination and Mitigation of CB Warfare Agents, Toxic Hazardous Materials, Viruses, Bacteria and Bacterial Spores," Technical Report, MOD2001-1008-M, Feb. 2001.
NASA Facts, "Four Propulsion Enhancements Planned for Space Shuttle Fleet by 2005," FS-2001-04-81-MSFC, May 2001.

* cited by examiner

*Primary Examiner*—Shailendra Kumar
(74) *Attorney, Agent, or Firm*—Luis M. Ortiz; Kermit D. Lopez; Ortiz & Lopez, PLLC

(57) ABSTRACT

Methods of and systems for remediating hydrazine spills, solutions and hydrazine-contaminated objects including areas thereof. Initially, an aqueous solution comprising a dicarbonyl-compound can be prepared. The aqueous solution can then be provided for application to an object contaminated with a hydrazine group compound. The hydrazine group compounds are converted to a stable organic compound as a result of a reaction of the dicarbonyl-compound and hydrazine group compound. Conversion assists in the remediation of the hydrazine group compound from the object. The stable organic compound produced as a result of the reaction between the dicarbonyl-compound and hydrazine group compound can then be treated with a metal catalyst and hydrogen to produce glutamine or a derivative thereof. Both the stable organic compound and glutamine can undergo microbiological degradation without further remedial intervention.

20 Claims, 4 Drawing Sheets

GLUTAMINE

300

400

700

702

| % 2KG | Temperature Rise in C |
|---|---|
| 13.4 | 19.5 |
| 18.19 | 29.5 |
| 22.0 | 37.5 |
| 24.56 | 39.0 |
| 28.3 | 45.5 |
| 34.1 | 56.0 |
| 41.53 | 62.5 |
| 7.62 | 10.0 |
| 0 | 0 |

704

METHODS AND SYSTEMS FOR REMEDIATING HYDRAZINE-CONTAMINATED EQUIPMENT AND/OR SURFACES

TECHNICAL FIELD

The present invention is generally related to decontamination and remediation methods and systems. The present invention is also related to hydrazine (Hz) and hydrazine-based compounds, such as monomethylhydrazine (MMH) or 1,1-dimethylhydrazine (UDMH). The present invention additionally relates to methods and systems for remediating hydrazine from hydrazine-contaminated objects, including hydrazine contaminated areas thereof. The present invention is also related to dicarbonyl compounds, including dialdehydes, diketones, aldehyde-ketones, aldehyde-acids, aldehyde-esters, keto-acids and keto-esters. The present invention is specifically related to the involvement of the following compounds in remediation of hydrazine: 2-ketoglutaric acid (2KG), 6-oxo-1,4,5,6-tetrahydro-pyridazine-3-carbonic acid (PCA), and glutamine.

BACKGROUND OF THE INVENTION

An environmentally conscious remediation process for the emergency treatment/disposal of hydrazine fuels spills is needed. The highly toxic hydrazine family of fuels is utilized as rocket propellants in virtually all U.S. space programs including both launch vehicles and satellite propulsion systems. Since large volumes of these fuels are annually shipped all over the United States, accidental major spills of these propellants could potentially occur near populated communities during transport over the nation's highways. In addition, smaller spills could also occur during launch operations and storage at the user facilities.

An inadvertent release of hydrazine to the environment can be extremely hazardous due to the mutagenic nature of such chemical compounds, which can induce tumor growth in human beings years following even a low level exposure. Hydrazine compounds are classified as suspected human carcinogens and their permissible levels of exposure have been reduced to 10 parts per billion (ppb). A hydrazine spill remediation process, to be developed, should not only destroy the propellant fuel but also should not generate other hazardous materials. An in-situ processing method involving direct application of the treatment reagent or process to the spill is preferred.

Currently, a small hydrazine spill, occurring at launch facilities, is washed down with water. The diluted water is treated with an oxidizing agent such as sodium hypochlorite or alternatively, the hydrazine containing water is transported to a hazardous waste facility for incineration. The former treatment method with UDMH is unsatisfactory in that a strong carcinogen, n-Nitrosodimethylamine, is generated. In addition, the hypochlorite oxidation of both UDMH and MMH yields volatile halogenated hydrocarbons, which are priority pollutants. In the case of a spill on soil, the contaminated material is transported for disposal at an incineration facility.

An accident involving a transport trailer may spill four to five thousand gallons of the hydrazine fuel, whereas a catastrophic failure of a fuel storage vessel at a launch facility may release twenty thousand gallons or more of the propellant. A rail car derailment resulting in a hydrazine (i.e., commercial use) release occurred in Southern California several years ago.

A major spill of a hydrazine transport trailer could potentially result in legal action amounting to millions of dollars. Additionally, minor hydrazine spills resulting from leaks or other causes are not unusual during space launch operations. These spills, which can result in evacuations and expensive launch delays, are washed down into the waste fuel tank for later disposal. A greater concern is a major accidental spill of a hydrazine transport trailer, occurring off-site during shipment of the propellant over the public highways. Although such an incident has not occurred to date, a treatment/disposal process should be developed and be available when needed. An environmentally conscious, inexpensive method for the complete conversion of the spilled hydrazine into innocuous materials is needed. This treatment process may entail chemical reactions, bioremediation, or other methods such as pyrolysis, photolysis, or catalysis.

Hydrazine group compounds, including hydrazine, monomethylhdrazine (MMH), and 1,1-dimethylhydrazine (UDMH), are widely used as fuels (e.g., in rocket propulsion systems and fighter jets), corrosion inhibitors (e.g., nuclear industry), catalysts, emulsifiers, or dyes. Hydrazine is typically utilized as a monopropellant in rocket propulsion applications because it can readily ignite when placed in contact with noble metal catalysts. Hydrazine is particularly popular with satellite companies because hydrazine, when used as a monopropellant, saves space, complexity and weight. Hydrazine and hydrazine-based compounds can also function as a precursors in the synthesis of a number of drugs, polymers, plasticizers and pesticides. As indicated above, however, hydrazine is also extremely toxic and dangerous. Note that as utilized herein, the term "hydrazine" is generally analogous to the chemical formula $N_2H_4$, while the term monomethylhdrazine (MMH) is generally analogous to the chemical formula $CH_3NHNH_2$.) Additionally, the term dimethylhydrazine (UDMH) can be referred to by the chemical formula $(CH_3)_2NNH_2$.

The U.S. Occupational Safety and Health Administration (OSHA), for example, requires the prevention of exposure to hydrazine and its derivatives at concentrations greater than one part per million (1.3 mg/m$^3$). Hydrazine and hydrazine derivatives are readily combustible reducing agents that react violently with oxidizing agents and thus present a serious safety hazard. Hydrazine and hydrazine derivatives are well known components of liquid rocket fuels in conjunction with an oxidizing agent such as dinitrogen tetroxide. Thus, at facilities where liquid-fueled rockets are prepared for flight, there is a particular need to provide reliable and sensitive methods and systems for decontaminating objects, such as fighter jets and maintenance equipment thereof, and exposed environments which can become contaminated with hydrazine. Ideally, such hydrazine remediation methods and systems should also have a limited, if negligible effect on the environment.

Many reactions of hydrazine with dicarbonyl compounds are known. For example, Gerd Kaupp and Jens Schmeyers have investigated hydrazine reactivity, as reported in "Solid-State Reactivity of the Hydrazine-Hydroquinone Complex," J. Phys. Org. Chem 2000, 13: pp. 388–394, which is incorporated herein by reference. Kaupp and Schmeyers investigated the solid-state reactivities of the hydrazine-hydroquinone 1:1 complex and of hydrazine hydrochloride with solid aldehydes, ketones, carboxylic acids, thiohydantoin and 4-nitrophenyl isothiocyanate. Kaupp and Schmeyers reported that only the hydrazine complex provides quantitative additions, condensations, ring openings and ring closures. The solid-state mechanisms were investigated by atomic force microscopy (AFM) and far-reaching anisotropic molecular movements were correlated with the crystal packing, both on the hydrazine complex surface and on the surface of two benzaldehydes. Based on this research Kaupp and Schmeyers concluded that the hydrazine can move into the aldehyde crystals for chemical reaction without melting. Kaupp and Schmeyers also reported that characteristic surface features could be created by common phase rebuilding and phase transformation on both the hydrazine-donating and -accepting crystals.

The present inventors have examined compounds that will react with hydrazine rapidly and quantitatively. The present inventors have investigated several compound classes in order to tailor these derivatives of hydrazine for facile detection (i.e., to required levels) by current analytical methods.

Decontamination methods and systems can be separated into three major categories: physical removal, chemical inactivation, or a combination of both physical and chemical means. Wiping, sweeping, scraping, blowing, vacuuming, rinsing with water, and steam cleaning are all examples of physical methods for the removal of contaminants. In many cases, physical removal of gross contamination is an initial step in decontamination and remediation thereof. Physical removal of gross contamination usually is not sufficient to reduce contaminant concentrations to background levels. In most cases, physical removal is followed by a wash and rinse process using cleaning solutions. These cleaning solutions often dissolve contaminants and keep them in a solution until they can be rinsed away. Rinsing removes contaminants from an affected object or area through the dual process of dilution and solubilization. Multiple rinses with clean water can remove more contaminants than a single rinse.

Despite use of present cleaning solutions and rinsing procedures, contaminants generally still persist after remediation, although in a diluted form, and can be relocated to areas surrounding the object or area targeted for decontamination. Such is the case where hydrazine is diluted and allowed to run off along a surface (e.g., earth or pavement) away from the decontamination zone, or worse is absorbed into the earth and into water aquifers.

More effective methods and systems are needed for remediating hydrazine from contaminated objects, solutions, and areas. The present inventors recognize this need and have invented method of and systems for hydrazine remediation.

BRIEF SUMMARY OF THF INVENTION

The following summary of the invention is provided to facilitate an understanding of some of the innovative features unique to the present invention, and is not intended to be a full description. A full appreciation of the various aspects of the invention can be gained by taking the entire specification, claims, drawings, and abstract as a whole.

It is therefore one aspect of the present invention to provide improved remediation methods and systems.

It is therefore another aspect of the present invention to provide methods and systems for remediating hydrazine from hydrazine contaminated objects and areas thereof.

It is yet an additional aspect of the present invention to provide an aqueous solution prepared from a dicarbonyl-compound.

It is yet an additional aspect of the present invention to provide a cleaning solution that includes a dicarbonyl-compound for converting hydrazine to a stable organic compound.

It is still an additional aspect of the present invention to treat a stable organic compound produced as a result of a reaction between a dicarbonyl-compound and a hydrazine with a metal catalyst and hydrogen to produce glutamine or a derivative thereof.

The above and other aspects of the invention can be achieved as will now be described. Methods and systems for remediating hydrazine from hydrazine-contaminated objects (including areas) are disclosed herein. Initially, an aqueous solution comprising a dicarbonyl-compound can be prepared. Such a dicarbonyl-compound can be, for example, 2-ketoglutaric acid. (Note that the term "dicarbonyl-compound" as utilized herein generally refers to a dialdehyde, diketone, aldehyde-ketone, aldehyde-add, aldehyde-ester, keto-acid and/or a keto-ester.) The aqueous solution can then be applied to an object contaminated with a hydrazine group compound, such that the hydrazine group compound is converted to a stable organic compound as a result of a reaction of the dicarbonyl-compound and hydrazine group compound in order to remediate the hydrazine group compound from the object. Such a hydrazine group compound can be, for example, hydrazine (Hz), monomethylhdrazine (MMH), or 1,1 dimethylhydrazine (UDMH).

The solution, which may be aqueous, can be applied to the object contaminated with the hydrazine group compound following an initial attempt at a physical removal (e.g., wiping, sweeping, scraping, blowing, vacuuming, rinsing with water, steam cleaning, etc.) of the hydrazine group compound from the area, object or solution. Alternatively, the aqueous solution can be applied directly to the object, thereby skipping this physical removal step. The solution can be prepared in the form of a cleaning solution. Application of such an aqueous or cleaning solution to the object can occur by rinsing the object with the solution. Finally, the stable organic compound produced as a result of the reaction between the dicarbonyl-compound and hydrazine group compound can then be treated by microbiological degradation or with a metal catalyst and hydrogen to produce glutamine or a derivative thereof. The glutamine can then be permitted to undergo microbiological degradation thereof.

BRIEF DESCRIPTION OF THE DRAWINGS

The accompanying figures, in which like reference numerals refer to identical or functionally-similar elements throughout the separate views and which are incorporated in and form part of the specification, further illustrate the present invention and, together with the detailed description of the invention, serve to explain the principles of the present invention.

DETAILED DESCRIPTION OF THE INVENTION

The particular values and configurations discussed in these non-limiting examples can be varied and are cited merely to illustrate an embodiment of the present invention and are not intended to limit the scope of the invention.

Figure 1:
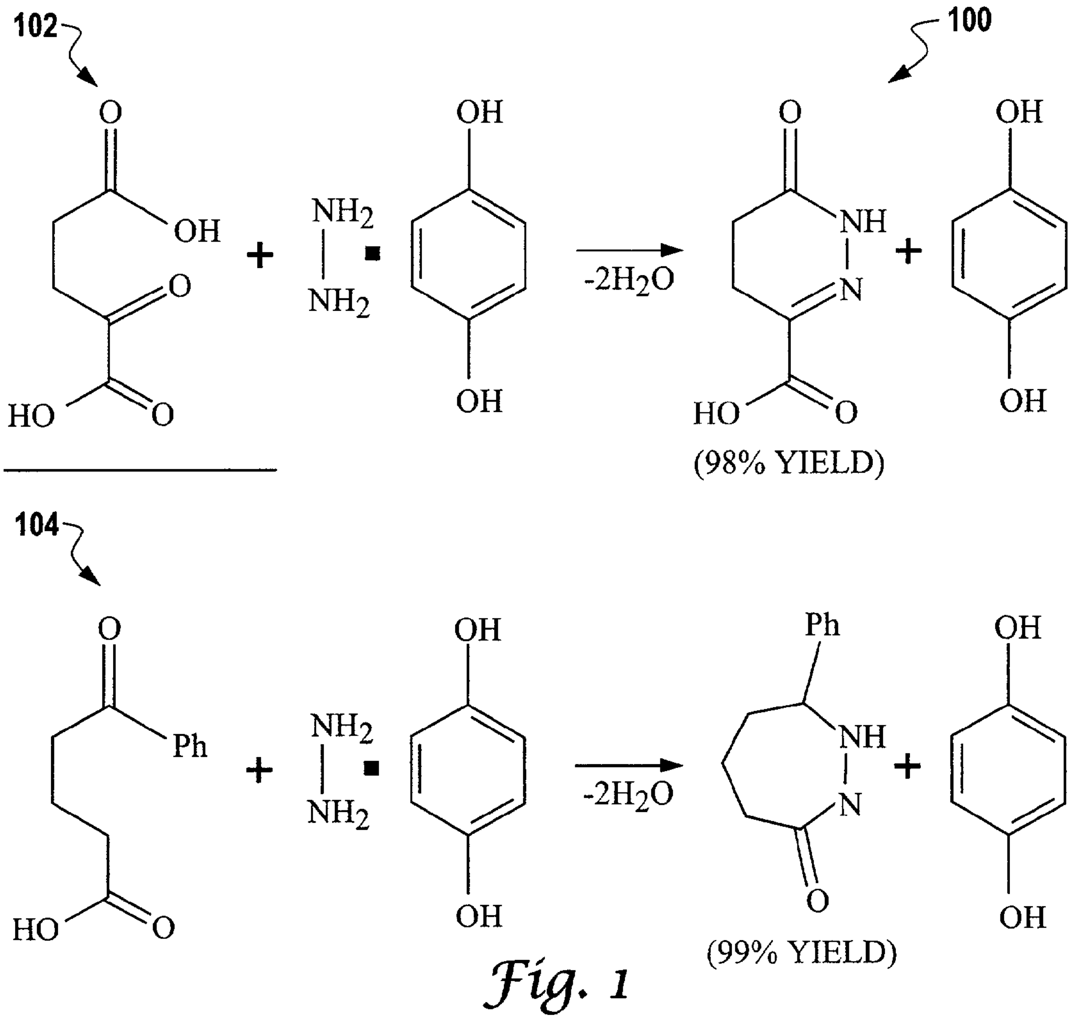
FIG. 1 illustrates a schematic diagram depicting a reaction between a dicarbonyl-compound and a complex of hydrazine.

FIG. 1 illustrates a schematic diagram 100 depicting a reaction between a dicarbonyl-compound and a complex of hydrazine. Two cases 102 and 104 are illustrated in FIG. 1. In each case, the solid compounds were ball milled at room temperature in a ratio of 2:1 (dicarbonyl-compound to hydrazine complex) and a near quantitative yield was obtained. The 6-oxo-1,4,5,6-tetrahydro-pyridazine-3-carbonic acid formed from the reaction of 2-ketoglutaric acid and the hydrazine complex comprises a high melting solid (i.e., melting point within a range of approximately 106° C.–198° C.).

Figure 2:
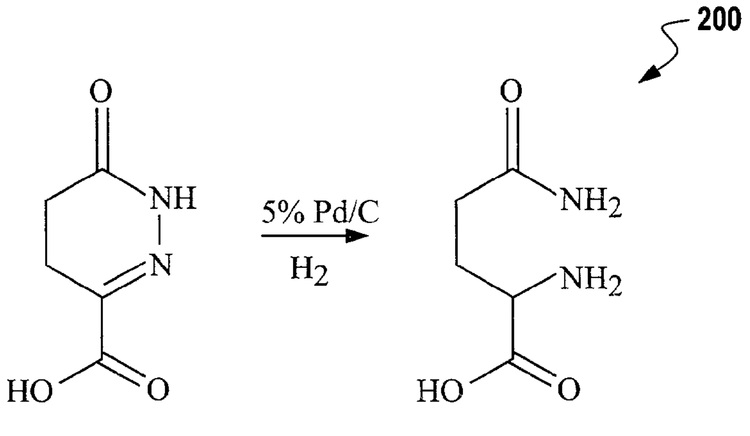
FIG. 2 depicts a schematic diagram illustrating a production of glutamine.

FIG. 2 depicts a schematic diagram 200 depicting the treatment of hydrazine waste to glutamine or a derivative thereof, in accordance with a preferred embodiment of the present invention. The hydrogenization of pyridazine using 5% Pd/C can provide glutamine in a 45% yield. Although this pyridazine is not easily biodegraded, the present inventors believe that glutamine can be utilized as a plant nutrient or that it is easily biodegradable. Glutamine can be specifically utilized as a source of energy and for nucleotide synthesis by all rapidly dividing cells. Thus, rather than acting as an environmental hazard, glutamine or a derivative can actually benefit plants exposed to it during a hydrazine remediation process, as described herein.

Figure 3:
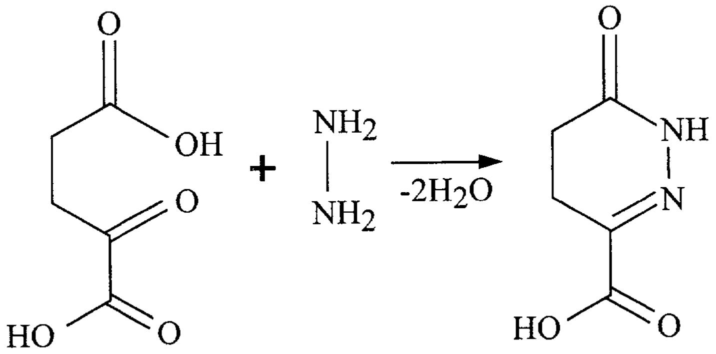
FIG. 3 illustrates a schematic diagram depicting a reaction of 2-ketoglutataric acid, which provides a near quantitative conversion of hydrazine to a 6-oxo-1,4,5,6-tetrahydro-pyridazine-3-carbonic acid, in accordance with a preferred embodiment of the present invention.

FIG. 3 illustrates a schematic diagram 300 depicting a reaction of 2-ketoglutataric acid, which provides a near quantitative conversion of hydrazine to a 6-oxo-1,4,5,6-tetrahydro-pyridazine-3-carbonic acid, a preferred embodiment of the present invention. In general, the chemical transformation depicted in schematic diagram 300 of FIG. 3 allows for the removal of hydrazine from aqueous solutions generated by the decontamination processes described herein. The reaction with concentrated hydrazine also can provide the desired product with some evolution of heat. The low solubility of the compound in water allows for the separation of most of this adduct by a simple filtration.

The MSDS for 6-oxo-1,4,5,6-tetrahydro-pyridazine-3-carbonic acid does not list any known acute toxicities and thus it should be a nonhazardous waste. However the ideal situation would be to find a method for the safe destruction or remediation of the 6-oxo-1,4,5,6-tetrahydro-pyridazine-3-carbonic acid. The use of microbes (e.g., a pseudomonas species found in the soil) as a method for the metabolism of a nitrogen-nitrogen bond can thus be implemented, in accordance with the methods and systems described herein. After about ten minutes thereafter, a white precipitate can be formed, which is generally characterized by Nuclear Magnetic Resonance to be the expected product, 6-oxo-1,4,5,6-tetrahydro-pyridazine-3-carbonic acid. The reaction generally appears to be a quantitative reaction with the aqueous hydrazine.

Figure 4:
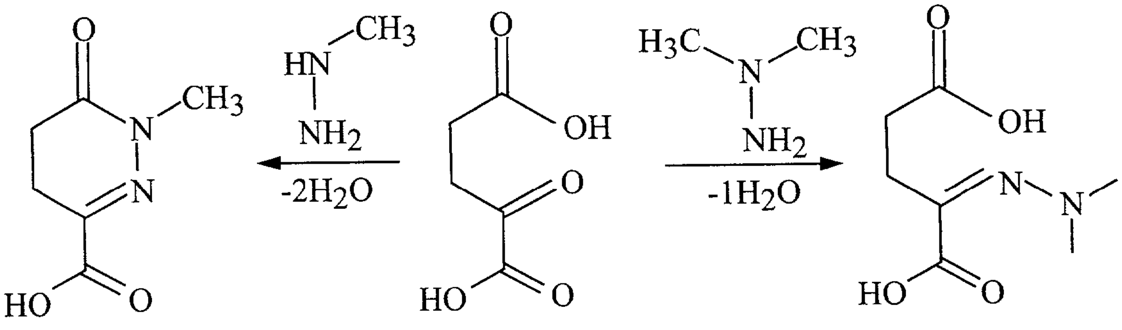
FIG. 4 depicts a schematic diagram illustrating the reaction of MMH and UDMH with 2-ketoglutaric aid followed by hydrogenation, in accordance with a preferred embodiment of the present invention.

FIG. 4 depicts a schematic diagram 400 illustrating the reaction of MMH and UDMH with 2-ketoglutaric aid followed by hydrogenation, in accordance with a preferred embodiment of the present invention. The schematic diagram 400 depicted in FIG. 4 can be implemented by adding a sample of the hydrazine derivative to a slight excess of an aqueous solution of 2-ketoglutaric acid. Note that the solution described herein (i.e., which includes a dicarbonyl-compound) can be prepared as aqueous solution or a non-aqueous solution, depending on particular desired applications. Thus, the use of an aqueous solution is not considered a limiting feature of the present invention. Rather the use of an aqueous solution represents merely one possible embodiment of the present invention. Non-aqueous solutions represent another possible embodiment of the present invention.

Figure 5:
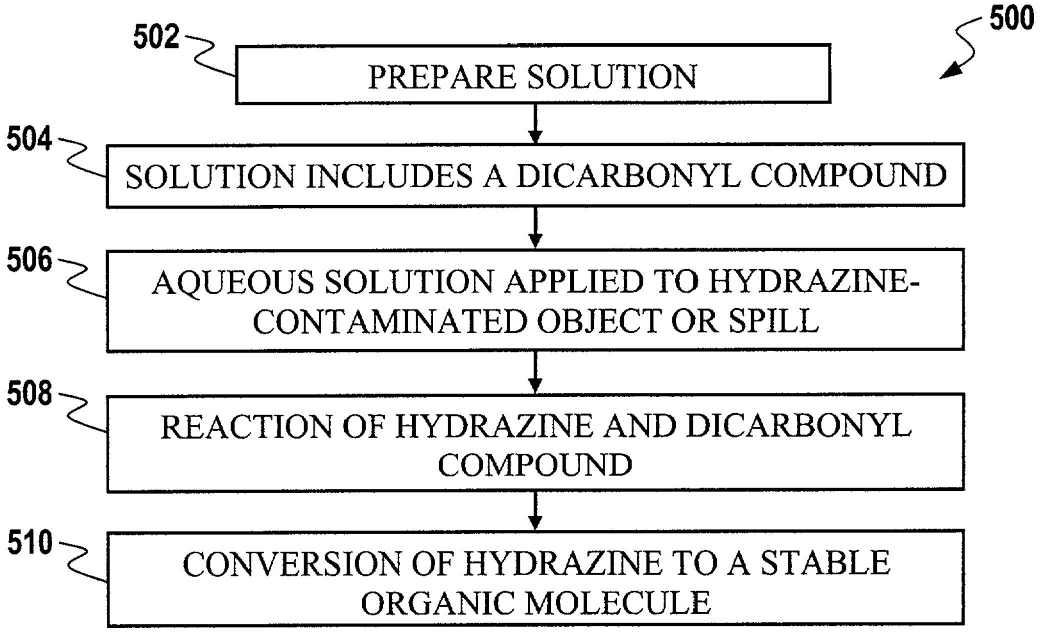
FIG. 5 illustrates a high-level flow chart of operations illustrating logical operational steps, which can be implemented in accordance with a preferred embodiment of the present invention.

FIG. 5 illustrates a high-level flow chart 500 of operational steps, which can be implemented in accordance with a preferred embodiment of the present invention. As illustrated at block 502, a solution can be prepared that includes, as indicated at next at block 504, a dicarbonyl-compound. Such a solution can be prepared in the form of a cleaning solution. The solution can be an aqueous solution or a non-aqueous solution. An example of a dicarbonyl-compound that can be utilized in accordance with the methods and systems of the present invention is a keto-acid, such as a 2-ketoglutaric acid. Once the solution has been prepared, it can provided for utilization in hydrazine remediation.

As indicated next at block 506, the solution as provided via processing of the operations described at blocks 502 and 504 can be applied to an object contaminated with a hydrazine group compound. Application can occur, for example, through a rinsing of the hydrazine contaminated object with the solution that includes the dicarbonyl-compound. Examples of hydrazine group compounds that may contaminate an object or area thereof can include simply hydrazine, MMH, or UDMH.

It can be appreciated by those skilled in the art that the application of the dicarbonyl compound solution to the hydrazine contaminated object and/or area (e.g., a hydrazine spill) thereof can take place following an initial attempt at a physical removal of the hydrazine group compound from the object or area thereof. As indicated previously, wiping, sweeping, scraping, blowing, vacuuming, rinsing with water, and steam cleaning are all examples of physical methods for the removal of contaminants. Such physical removal techniques can thus occur in tandem with the application of the dicarbonyl-compound solution described herein.

A reaction can then occur, as illustrated at block 508 between the hydrazine group compound and the dicarbonyl-compound. As a result of this reaction, the hydrazine group compound is converted to a stable organic compound, as indicated at block 510, in order to remediate the hydrazine group compound from the object. Thus, based on the foregoing it can be appreciated that the present invention allows for the use of a solution of a dicarbonyl-compound (e.g. 2-ketoglutaric acid) for the treatment of hydrazine waste. Prior art solutions for the treatment of hydrazine generally involve solubilization and dilution processes. The hydrazine remediation methods and systems described herein do not only involve solubilization and dilution. Rather, the present invention involves a conversion of hydrazine to a stable organic compound. Such a conversion can occur after application of the dicarbonyl-compound solution through the use of solubilization and dilution processes, among others. Note that the step of treating a stable organic compound with a metal catalyst and hydrogen to produce glutamine, can also includes the step of producing a derivative of glutamine, rather than simply glutamine.

Figure 6:
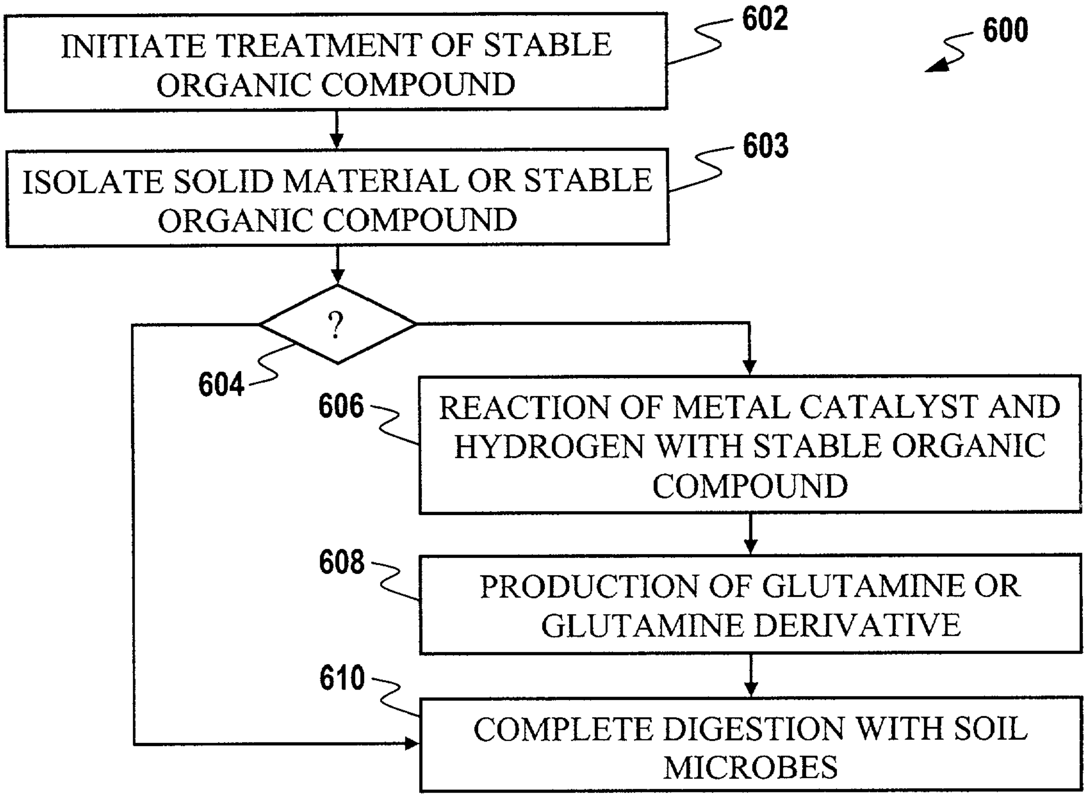
FIG. 6 depicts a high-level flow chart of operations illustrating logical operational steps, which can be implemented in accordance with a preferred embodiment of the present invention.

FIG. 6 depicts a high-level flow chart 600 of operations illustrating logical operational steps, which can be implemented in accordance with a preferred embodiment of the present invention. Once the stable organic compound has been created as a result of the reaction between hydrazine and the dicarbonyl-compound, the stable organic compound can be treated with a metal catalyst and hydrogen to produce glutamine and/or a derivative thereof.

Thus, as indicated at block 602, treatment of the stable organic compound can be initiated. The compound (or solid material formed thereof) can be isolated as indicated at block 603. A decision can be made, as indicated at block 604, to determine whether or not the stable organic, should be treated at another location, or treated directly, as indicated by processes described at blocks 606 to 610. If it is determined to isolate the stable organic compound for treatment at another location, then the operation indicated at block 610 can be processed elsewhere. As indicated at block 610, any remaining material (i.e., the stable organic compound) can simply be digested via soil microbes.

If necessary, however, the stable organic compound can be treated with a metal catalyst and hydrogen as illustrated at block 606, which follows decision block 604. As depicted at block 606, a reaction can occur between the metal catalyst and hydrogen and the stable organic compound. As a result of this reaction, glutamine or a glutamine derivative can be produced, as depicted at block 608. Finally, as illustrated at block 610 complete digestion with soil microbes can occur. For example, the reaction of hydrazine with a 2-ketoglutaric acid, followed by hydrogenation, can yield glutamic acid, a compound, which has been utilized to enhance fertilizer use.

A system for remediating hydrazine in accordance with the present invention thus generally includes a solution that can be formed from a dicarbonyl-compound, and an application mechanism for applying the solution to an object or area (e.g., a spill) contaminated with a hydrazine group compound. A dicarbonyl-compound can be implemented as a solution (e.g. an aqueous solution), which can then be applied to an object or area contaminated with a hydrazine group compound. Such a hydrazine group compound can include at least one of the following: hydrazine (Hz), monomethylhdrazine (MMH), and 1,1 dimethylhydrazine (UDMH). The application mechanism itself can be implemented as a rinsing mechanism for rinsing the object contaminated with the hydrazine group compound with the solution. Such a rinsing mechanism can be, for example, a hose or other fluid delivery device and/or system. The application mechanism can also be implemented in the form of objects or devices such as sponges, pads, spray bottles, and so forth. A metal catalyst and hydrogen can thus be applied to the contaminated objects with the application mechanism to produce glutamine thereof.

Figure 7:
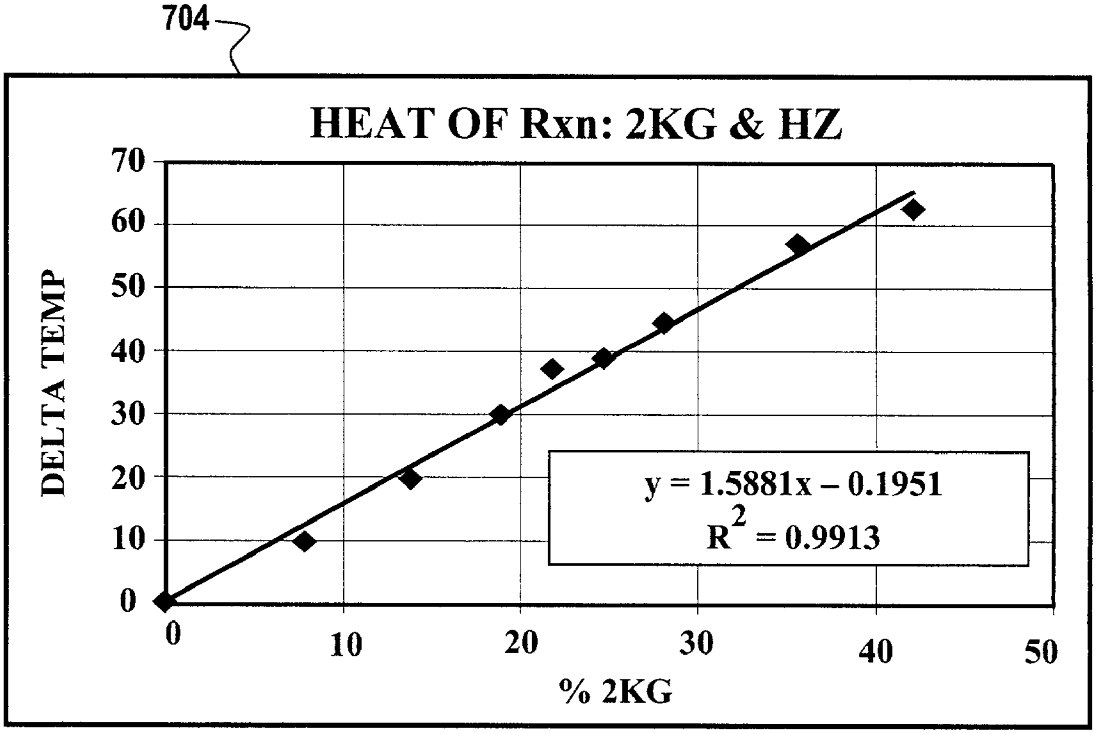
FIG. 7 illustrates a plot of experimental data, which can be collected in accordance with an alternative embodiment of the present invention.

FIG. 7 illustrates a plot 700 of experimental data, which can be collected in accordance with an alternative embodiment of the present invention. Note that a graph 704 is associated with chart 702, which depicts such experimental data. Note that the experimental techniques utilized to collect the data depicted in FIG. 7 represent merely one possible embodiment of the present invention. Those skilled in the art can appreciate than many other embodiments can be implemented. An insulated reaction vessel can be utilized to insure that heat evolution will not be underestimated. A 1-cup Styrofoam™ cup equipped with stir bar and thermometer, 75 mL of 2-ketoglutaric acid solution can be added and stirred a few minutes before the addition of a 1.1 eq of hydrazine monohydrate. The temperature can be monitored at 30 sec to 1-minute intervals for 15 minutes. After about 45 seconds, seed crystals of 6-oxo-1,4,5,6-tetrahydropyridazin-3-carboxylic acid can be added to the solution; otherwise two exotherms can be observed (i.e., one large temperature rise immediately and second smaller one after about 10 minutes associated with the heat of crystallization). Initial temperatures can be about 18° C., and the highest final temperature can be approximately 84° C., although the some boiling occurred in the mixing zone as the hydrazine can be added to the 41.5% 2-ketoglutarate solution.

Hydrazine monohydrate (98%), deuterium oxide and dimehtylsulfoxide-$d_6$ can be utilized, along with 6-oxo-1,4,5,6-tetrahydropyridazin-3-carboxylic acid (97%) and 2-ketoglutaric acid (98%) to produce the following results. The reaction of solid 2-ketoglutaric acid with hydrazine monohydrate can generally be produced as follows: A 2-ketoglutarate (450 mg) can be combined with hydrazine monohydrate (70 μL), which produces heat immediately. Extraction of the reaction residue with water may only partially dissolved the solid, and the solution provided an NMR spectrum consistent with unreacted starting material and the expected product. The remaining solid can be dissolved in a mixture of MeOH, chloroform and DMSO, and can possess NMR spectra consistent with the expected product.

Note that a product from one of the aforementioned reactions can be derived with N,N-bis(trimethylsilyl)trifluroacetamide at room temperature and analyzed by both EI and CI mass spectrometry. In the EI spectrum, several chromatographic peaks can be observed with the largest corresponding to the 6-oxo-1,4,5,6-tetrahydropyridazin-3-carboxylic acid. One peak can be viewed for in a CI chromatogram with a mass spectrum dominated by 287 m/z (M+1). The mass balance of the product can be high and the melting point low, presumably owing to inclusion of the hydrazinium salt of the product. Addition of a 10% equivalent of 2-ketoglutaric acid to consume excess hydrazine, and recrystalization from hot water can afford a material with the same melting point as the standard material, 194–196° C. NMR chemical shifts can vary with concentration and pH, and are generally identical to the standard material: H (δ, $D_2O$, MeOH ref. 3.30 ppm, 300 MHz) 2.56 (2H, t, $J_{H\text{-}H}$ 8.9 Hz), and 2.85 (2H, t, 8.9 Hz) ppm; $^{13}C$ (δ, $D_2O$, MeOH set to 49.0 ppm, 75 MHz) 20.6, 24.9, 146.0, 166.1, and 170.9 ppm.

The present invention offers a number of advantages. The removal of hydrazine according to the methods and systems described herein will allow for the remediation of hydrazine to useful by-products or biodegradable forms, which not only provide environmental benefits, but also reduces the cost of hydrazine waste disposal. The methods and systems described here can be utilized at airports, military facilities, and rocket launches and space vehicle-landing pads (e.g., the Space Shuttle). In particular, the present invention can also find use in orbiting facilities such as the International Space Station in which hydrazine exposure can be problematic. The present invention has particularly useful applications to wash water cleanup and spill abatement.

The embodiments and examples set forth herein are presented to best explain the present invention and its practical application and to thereby enable those skilled in the art to make and utilize the invention. Those skilled in the art, however, will recognize that the foregoing description and examples have been presented for the purpose of illustration and example only. Other variations and modifications of the present invention will be apparent to those of skill in the art, and it is the intent of the appended claims that such variations and modifications be covered. The description as set forth is not intended to be exhaustive or to limit the scope of the invention. Many modifications and variations are possible in light of the above teaching without departing from the spirit and scope of the following claims. It is contemplated that the use of the present invention can involve components having different characteristics. It is intended that the scope of the present invention be defined by the claims appended hereto, giving full cognizance to equivalents in all respects.

The invention claimed is:

1. A method for neutralizing harmful effects of hydrazine contamination, said method comprising the steps of:

providing an aqueous solution comprising a 2-ketoglutaric acid, said solution adapted for application to hydrazine contaminated equipment and/or ground surfaces; and applying said solution to equipment and/or ground surfaces contaminated with a hydrazine group compound, wherein said hydrazine group compound is converted to a stable organic compound as a result of a reaction between said solution comprising said 2-ketoglutaric acid and said hydrazine group compound.

2. The method of claim 1 wherein the step of applying said solution to an equipment and/or ground surfaces contaminated with a hydrazine group compound, further comprises the step of:

applying said aqueous solution to said object contaminated with said hydrazine group compound following physical removal of debris also contaminated with said hydrazine group compound from said equipment and/or ground surfaces.

3. The method of claim 1 wherein the step of applying said aqueous solution to an equipment and/or ground surfaces contaminated with a hydrazine group compound, further comprises the step of:

using an application mechanism to rinse said equipment and/or ground surfaces contaminated with said hydrazine group compound with said aqueous solution.

4. The method of claim 1 further comprising the step of:

treating said stable organic compound with a metal catalyst and hydrogen to produce glutamine thereof, wherein said hydrazine group compound is converted to a stable organic compound as a result of a reaction of said 2-ketoglutaric acid and hydrazine group compound.

5. The method of claim 1 wherein said hydrazine group compound comprises monomethylhdrazine (MMH).

6. The method of claim 1 wherein said hydrazine group compound comprises 1,1 dimethylhydrazine (UDMH).

7. The method of claim 1 wherein said aqueous solution is a cleaning solution.

8. A method for treating hydrazine contaminated equipment and/or ground surfaces comprising the steps of:

providing a cleaning solution that includes 2-ketoglutaric acid; and rinsing at least one of equipment or ground surfaces contaminated by a hydrazine group compound with said cleaning solution.

9. A method using a dicarbonyl-compound for decontaminating equipment and/or ground surfaces accidentally contaminated in an operational environment or during an operational activity with a hydrazine group compound, said method comprising the steps of:

providing an application mechanism adapted to manage use of an aqueous cleaning solution said aqueous cleaning solution comprising 2-ketoglutaric acid; and applying said aqueous cleaning solution to equipment and/or ground surfaces contaminated with a hydrazine group compound, wherein said hydrazine group compound is converted to a stable organic compound as a result of a chemical reaction between said aqueous solution and said hydrazine group compound.

10. A system for treating hydrazine-contammated equipment or groundsurfaces, said system comprising:

an aqueous solution comprising a 2-ketoglutaric acid; and an application mechanism for enabling a user to manage the application of said aqueous solution to equipment or ground surfaces accidentally contaminated with a hydrazine group compound, wherein said hydrazine group compound is converted to a stable organic compound as a result of a reaction between said aqueous solution comprising said dicarbonyl-compound and said hydrazine group compound.

11. The system of claim 10 wherein said hydrazine group compound comprises includes at least one of the following: hydrazine (Hz), monomethylhdrazine (MMH), and 1,1 dimethylhydrazine (UDMH).

12. The system of claim 10 wherein said application mechanism further comprises:

a rinsing mechanism for rinsing said object contaminated with said hydrazine group compound with said aqueous solution.

13. The system of claim 10, further comprising a metal catalyst and hydrogen, said metal catalyst and hydrogen is applied to said contaminated objects with said application mechanism to produce glutamine thereof.

14. The system of claim 13 wherein said hydrazine group compound comprises at least one of the following: hydrazine (Hz), monomethylhdrazine (MMH), and 1,1 dimethylhydrazine (UDMH).

15. The system of claim 10 wherein said hydrazine group compound comprises hydrazine.

16. The system of claim 1 wherein said hydrazine group compound comprises monomethylhdrazine (MMH).

17. The method of claim 10 wherein said hydrazine group compound comprises 1,1 dimethylhydrazine (UDMH).

18. The system of claim 10 wherein said aqueous solution comprises a cleaning solution.

19. A system for remediating equipment and/or ground surfaces contaminated with hydrazine, said system comprising:

a cleaning solution comprising a 2-ketoglutaric acid;

a metal catalyst and hydrogen; and a rinsing mechanism for rinsing said equipment and/or ground surfaces contaminated with a hydrazine group compound with said cleaning solution, said metal catalyst and said hydrogen.

20. A system for decontaminating equipment and/or ground surfaces contaminated with a hydrazine group compound, said system comprising:

an aqueous solution managed by an application mechanism and comprising 2-ketoglutaric acid; and an application mechanism for enabling a user in the application of said aqueous solution to equipment and/or ground surfaces accidentally contaminated with a hydrazine group compound, wherein said hydrazine group compound is converted to a stable organic compound as a result of a reaction between said aqueous solution comprising said 2-ketoglutaric acid and said hydrazine group compound.

* * * * *